United States Patent
Wegener et al.

(10) Patent No.: US 11,850,347 B2
(45) Date of Patent: *Dec. 26, 2023

(54) SYSTEMS AND METHODS FOR AUTOMATED RECOVERY OF WHITE BLOOD CELLS AFTER PRODUCING A LEUKO-REDUCED BLOOD PRODUCT

(71) Applicant: Fenwal, Inc., Lake Zurich, IL (US)

(72) Inventors: Christopher J. Wegener, Libertyville, IL (US); Benjamin E. Kusters, Pleasant Prairie, WI (US)

(73) Assignee: Fenwal, Inc., Lake Zurich, IL (US)

( * ) Notice: Subject to any disclaimer, the term of this patent is extended or adjusted under 35 U.S.C. 154(b) by 232 days.

This patent is subject to a terminal disclaimer.

(21) Appl. No.: 17/128,377

(22) Filed: Dec. 21, 2020

(65) Prior Publication Data
US 2021/0106747 A1 Apr. 15, 2021

Related U.S. Application Data

(63) Continuation of application No. 14/463,095, filed on Aug. 19, 2014, now Pat. No. 10,905,819.

(51) Int. Cl.
*A61M 1/34* (2006.01)
*B01D 33/06* (2006.01)
(Continued)

(52) U.S. Cl.
CPC ............ *A61M 1/38* (2013.01); *A61M 1/0209* (2013.01); *A61M 1/3472* (2013.01);
(Continued)

(58) Field of Classification Search
CPC .. F01M 11/03; B01D 35/005; B01D 46/2414; B01D 36/006; B01D 29/88; B01D 29/21; B01D 35/153; B01D 35/16; B01D 2201/295; B01D 29/94; B01D 24/38; B01D 24/44; B01D 2201/291; B01D 33/0006; B01D 33/06; B01D 61/24; B01D 61/243; B01D 19/0052; A61M 1/38;
(Continued)

(56) References Cited

U.S. PATENT DOCUMENTS

| 3,896,733 A | 7/1975 | Rosenberg |
| 5,989,441 A | 11/1999 | Rashidbaigi et al. |

(Continued)

FOREIGN PATENT DOCUMENTS

| EP | 2548591 A1 | 3/2011 |
| WO | WO02/056992 A1 | 7/2002 |
| WO | WO2012125472 A1 * | 9/2012 |

OTHER PUBLICATIONS

Blood Donor Leukocyte Reduction Filters as a Source of Human B Lymphocytes, dated Sep. 2001; Benchmarks Bio Techniques, Sep. 2001; p. 31:464-466, vol. 31.

(Continued)

*Primary Examiner* — Pranav N Patel
(74) *Attorney, Agent, or Firm* — Cook Alex Ltd.

(57) ABSTRACT

The present disclosure relates to systems and methods for the separation of blood into blood products and, more particularly, to systems and methods that permit automated recovery of white blood cells after producing a leukocyte-reduced blood product.

11 Claims, 7 Drawing Sheets

(51) Int. Cl.
  *A61M 1/02* (2006.01)
  *A61M 1/36* (2006.01)
  *A61M 1/38* (2006.01)
  *B01D 19/00* (2006.01)
  *B01D 61/24* (2006.01)

(52) U.S. Cl.
  CPC ........ *A61M 1/3496* (2013.01); *A61M 1/3633* (2013.01); *A61M 1/3643* (2013.01); *A61M 1/3644* (2014.02); *A61M 1/0218* (2014.02); *A61M 1/3627* (2013.01); *A61M 2202/0439* (2013.01); *B01D 19/0052* (2013.01); *B01D 33/06* (2013.01); *B01D 61/24* (2013.01); *B01D 61/243* (2013.01)

(58) Field of Classification Search
  CPC .... A61M 1/0213; A61M 1/3627; A61M 1/02; A61M 1/0218; A61M 1/3644; A61M 1/3633; A61M 1/265; A61M 1/3496; A61M 1/0209; A61M 1/3643; A61M 2202/0439; A61M 1/3683; A61M 1/3686; A61M 1/3692; A61M 1/3693; A61M 1/3696; A61M 1/3472
  See application file for complete search history.

(56) References Cited

U.S. PATENT DOCUMENTS

| | | |
|---|---|---|
| 6,045,701 A | 4/2000 | Ung-Chhun et al. |
| 6,527,957 B1 | 3/2003 | Deniega et al. |
| 2005/0205498 A1 | 9/2005 | Sowemimo-Coker et al. |

OTHER PUBLICATIONS

A. Teleron, B. Carlson, P. Young; Blood Donor White Blood Cell . . . Progenitor Cells, Transfusion Jan. 2005, p. 21-25, vol. 45; Transplantation and Cellular Engineering.

S. Neron, N. Dussault, C. Racine; Whole-Blood Leukoreduction Filters . . . Peripheral Blood Lymphocytes, Transfusion; Apr. 2006; p. 537-544; vol. 46; Transplantation and Cellular Engineering.

S. Ebner, S. Neyer et al.; Generation of Large Numbers of Human . . . an Alternative to Standard Buffy Coats; Journal of Immunological Methods 252 (2001); pp. 93-104.

European Search Report and Search Opinion for counterpart application No. EP 15 18 1322 dated Jan. 20, 2016.

* cited by examiner

SYSTEMS AND METHODS FOR AUTOMATED RECOVERY OF WHITE BLOOD CELLS AFTER PRODUCING A LEUKO-REDUCED BLOOD PRODUCT

FIELD OF THE DISCLOSURE

The present disclosure relates to systems and methods for the separation of blood into blood products and, more particularly, to systems and methods that permit automated recovery of white blood cells after producing a leukocyte-reduced blood product.

BACKGROUND

The separation of blood into its components is commonly performed in apheresis procedures, in which blood components are separated while a donor or patient is connected to a separation system (sometimes referred to as a "chairside" procedure), or with previously-collected whole blood, in whole blood manufacturing or component processing procedures (sometimes referred to as a "backlab" procedure). For example, a common procedure is the separation of whole blood into plasma and red blood cells.

Such separation procedures are typically highly automated, utilizing a single-use fluid circuit comprising containers of various solutions, such as saline, anticoagulant and additive solution, as well as containers for the receipt of the separated blood components, all of which are interconnected by fluid flow paths in the form of tubing to a separation device, such as a centrifuge or a spinning membrane separator. The fluid circuit is associated with a durable hardware component which has pumps and clamps associated therewith that operatively engage the tubings to circulate the blood and its separated components through the associated single-use fluid circuit. The durable hardware component includes a programmable controller to automatically operate the pumps, clamps and separator in accordance with the desired apheresis procedure.

During blood separation procedures, leukoreduction is now widely performed, particularly with respect to separated red blood cells. Such leukoreduction is typically accomplished by flowing the separated red blood cells through a leukoreduction filter that captures the white blood cells. The used leuko filters have commonly been discarded. However, it has been recognized that the white blood cells retained in the used leuko filters can be isolated and used for research or therapeutic purposes. See, e.g., Amylynn A. Teleron, et al., "Blood donor white blood cell reduction filters as a source of human peripheral blood-derived endothelial progenitor cells," *Transfusion*, Vol. 45, p. 21, January 2005, which describes using a 30-mL syringe to back-flush human blood donor WBC reduction filters obtained from the American Red Cross with phosphate-buffered saline (PBS).

While the blood separation procedures have been highly automated, the recovery of white blood cells from the used leukoreduction filters has typically been accomplished using manual methods, such as that described in the above-referenced article. Thus, there is a need to provide automated systems and methods for the recovery of white blood cells from the leukoreduction filter associated with the single-use fluid circuit as part of the overall blood separation procedure.

SUMMARY

The present subject matter has a number of aspects which may be used in various combinations, and the disclosure of one or more specific embodiments is for the purpose of disclosure and description, and not limitation. This summary highlights only a few of the aspects of this subject matter, and additional aspects are disclosed in the drawings and the more detailed description that follows.

The subject matter has three basic aspects: a single-use fluid circuit that is configured to facilitate the automated recovery of leukocytes during an blood separation procedure; a system including a durable hardware component and the single-use fluid circuit for the automated recovery of leukocytes during a blood separation procedure; and a method for the automated recovery of leukocytes that utilizes the system and associated fluid circuit.

In keeping with the first basic aspect, a single-use fluid circuit for recovering leukocytes in conjunction with separation of biological fluid into two or more components is provided. As used herein, the terms "biological fluid," "blood" and "blood product" are intended to be comprehensive, and inclusive of whole blood and selected blood components (white blood cells, red blood cells, platelets and plasma) and combinations thereof, with or without any additional fluids, such as saline, anticoagulant and preservative solution. In one example, the biological fluid may be whole blood that is to be separated into plasma and red blood cells. The fluid circuit comprises separator that has an inlet for receiving the biological fluid, a first outlet for a separated first component (e.g., red blood cells), and a second outlet for a separated second component (e.g., plasma). The circuit also includes a leukocyte reduction filter having an inlet and an outlet.

A first fluid flow path is provided that is in fluid communication with the inlet of the separator and is configured to be connected to a source of biological fluid. The source may be a container of a previously collected biological fluid (as in a "backlab" procedure), or the source may be a donor or patient (as in a "chairside" procedure). A second fluid flow path is provided for connecting the first outlet of the separator to the inlet of the leukocyte reduction filter; a first collection container is provided for receiving leukocyte-reduced first component (e.g., red blood cells); and third fluid flow path is provided for connecting the outlet of the leukocyte reduction filter to the first collection container.

A source of solution (such as additive or preservative solution) is provided that is in fluid communication with the first fluid flow path through a fourth fluid flow path and in fluid communication with the second fluid flow path through a fifth fluid flow path.

A source of eluate is provided that is in fluid communication with the outlet of the leukocyte reduction filter through a sixth fluid flow path in fluid communication with the third fluid flow path. A second collection container is provided that is in fluid communication with the fifth fluid flow path through a seventh fluid flow path for receipt of recovered leukocytes.

In a further aspect, the fluid circuit comprises a third collection container for the separated second component (e.g., plasma) that is in fluid communication with the second outlet of the separator through an eighth fluid flow path.

In another aspect of the fluid circuit, the separator is a spinning membrane separator. Preferably, the spinning membrane separator comprises a housing having a top and a bottom, with the inlet being located adjacent the bottom of the housing and the first and second outlets being located adjacent the top of the housing.

In keeping with the second basic aspect, a system is provided for recovering leukocytes in conjunction with the separation of a biological fluid comprising blood into a first component comprising red blood cells and a second component comprising plasma. The system comprises a single-use fluid circuit having various of the aspects set forth above. In addition, the system comprises a durable hardware component with which the fluid circuit is associated. The durable hardware component comprises a plurality of clamps and pumps for selectively permitting fluid flow through the fluid circuit and a programmable controller for selectively opening and closing the clamps and actuating the pumps.

In one embodiment, the clamps selectively permit flow from the source of blood to the first fluid flow path, from the source of solution to the fifth fluid flow path, from the seventh fluid flow path to the fifth fluid flow path, from the seventh fluid flow path to the fifth fluid flow path, from the third fluid flow path to the first container, and from the sixth fluid flow path to the third fluid flow path. Such clamps may be two-way clamps associated with each of the first, third, fourth, fifth, sixth and seventh fluid flow paths. Alternatively, the clamps may comprise a first three-way clamp associated with the first and fourth fluid flow paths, a second three-way clamp associated with the third and sixth fluid flow paths, and a third three way clamp associated with the fifth and seventh fluid flow paths.

The pumps may comprise a first pump associated with the first fluid flow path, a second pump associated with the second fluid flow path, and a third pump associated with the fifth fluid flow path.

In keeping with the third basic aspect, a method is provided for recovering leukocytes in conjunction with the separation of blood into one or more components (such as plasma and red blood cells) using a system such as that having the various aspects set forth above. The method comprises three sub-procedures. The first sub-procedure separates a first blood component (such as red blood cells) from the blood, leukoreduces the first component, and collects the leuko-reduced first component in a first container. The second sub-procedure rinses the flow path using the solution. The third sub-procedure backwashes the leukocyte-reduction filter and collects the leukocytes recovered from the filter in a second container.

More particularly, the first component collection sub-procedure comprises: flowing the blood through the first fluid flow path to the inlet of the separator; flowing the first blood component from the first outlet of the separator through the second fluid flow path and flowing solution (such as an additive or preservative solution) from the fifth fluid flow path to the second fluid flow path; flowing the combined first blood component and solution through the second fluid flow path to the inlet of the leukocyte-reduction filter; and flowing the leukocyte-reduced first blood component from the outlet of the leukocyte-reduction filter through the third fluid flow path to the first collection container.

The second rinse sub-procedure comprises: flowing solution through the fourth fluid flow path into the first fluid flow path and to the inlet of the separator; then flowing the solution out the first outlet of the separator through the second fluid flow path to the inlet of the leukocyte reduction filter; then flowing the solution out the outlet of the leukocyte-reduction filter to the first collection container.

The third leukocyte-recovery sub-procedure comprises: flowing eluate through the sixth fluid flow path into the third fluid flow path and then into the outlet of the leukocyte-reduction filter; then flowing the eluate and recovered leukocytes out the inlet of the leukocyte-reduction filter through the second fluid flow path and into the fifth fluid flow path; then flowing the combined eluate and recovered leukocytes from the fifth fluid flow path through the seventh fluid flow path and into the second collection container. Non-limiting examples of the eluate include saline (preferably phosphate buffered saline or "PBS) and Pall Leukocyte Recovery Solution.

These and other more particular aspects of the present subject matter are set forth in the following description and accompanying drawings.

DETAILED DESCRIPTION OF THE EMBODIMENTS

A more detailed description of the fluid circuit, system and method in accordance with the present disclosure is set forth below. It should be understood that this description of specific circuits, systems and methods is intended to be exemplary, and not exhaustive of all possible variations and applications. Thus, the scope of the disclosure is not intended to be limiting, and should be understood to encompass variations or embodiments that would occur to persons of ordinary skill.

In general terms, a fluid circuit, system and method are provided for recovering leukocytes in conjunction with the separation of blood into one or more selected components. The method utilizes a single-use fluid circuit comprising a separator interconnected by tubing to various sources of solutions and collection containers in conjunction with a durable hardware unit comprising pumps and clamps that are automatically operated by a programmable controller. While the fluid circuit, system and method are described in the context of a procedure in which whole blood is separated into red blood cells and plasma, it should be appreciated that the recovery of leukocytes described herein may also be utilized in the context of producing other blood products, such as leuko-reduced platelet rich plasma or platelets.

As noted above, the method comprises three sub-procedures, each of which is automatically performed by means of the programmable controller. The first sub-procedure separates a selected first blood component from the blood, leukoreduces the first blood component, and collects the leuko-reduced first blood component in a first container. (In a typical RBC collection procedure, the separated plasma is also received in a collection container, but could optionally be returned to the donor in a chairside procedure.) The second sub-procedure rinses the flow path, using a solution, such as an additive or preservative solution used during the collection of the first blood component. The third sub-procedure backwashes the leukocyte-reduction filter with an eluate, such as saline (preferably PBS), and collects the leukocytes recovered from the filter in a second container.

Figure 1:
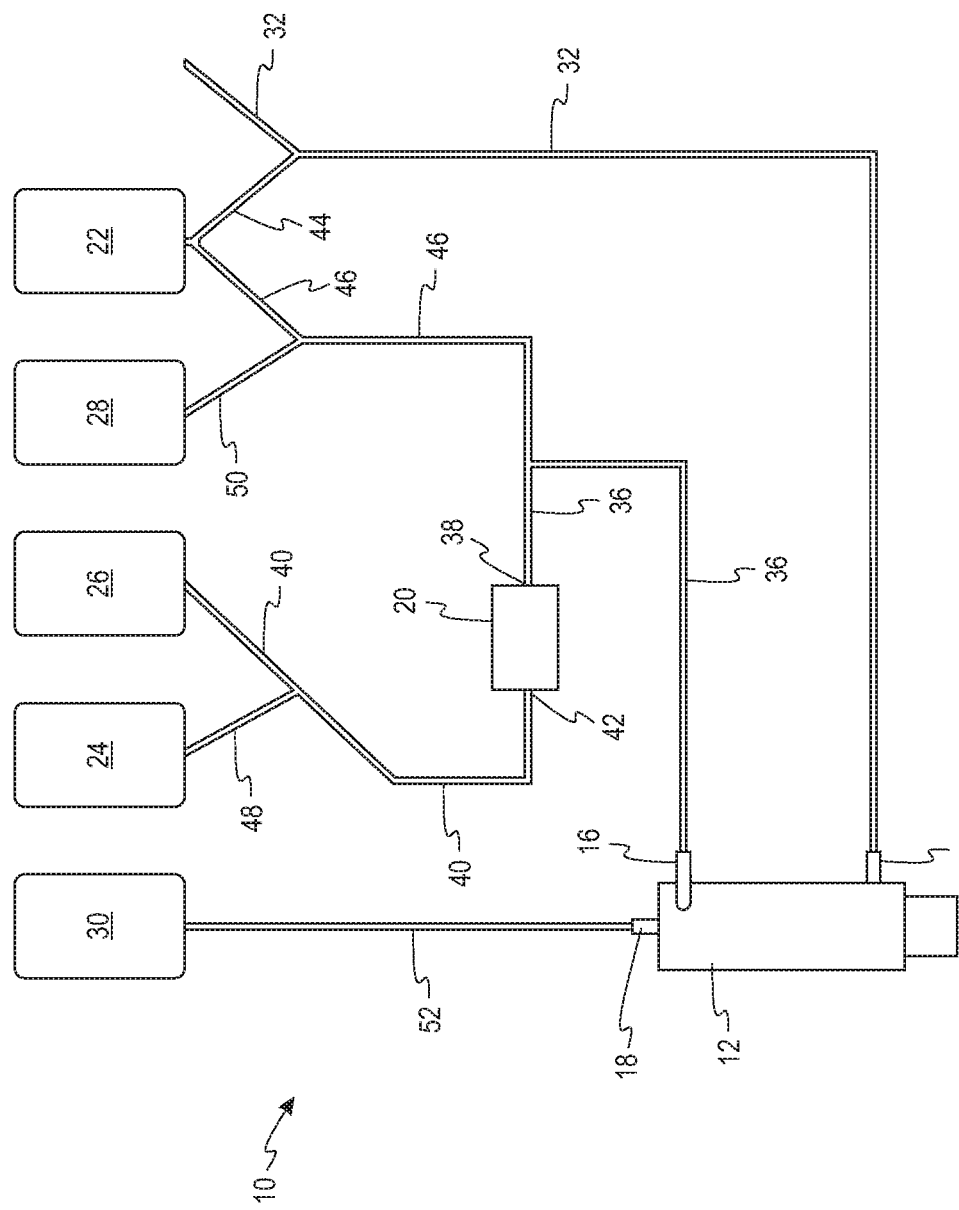
FIG. 1 is a schematic view of a single-use fluid circuit in accordance with the present disclosure.

Turning to FIG. 1, there is seen a single-use fluid circuit, generally designated 10, suited for use in a collection procedure for a leukocyte-reduced first blood component (e.g., RBCs) and a second blood component (e.g., plasma) in which the leukocytes separated from the first blood component are also automatically recovered. The fluid circuit is preferably fully pre-assembled and pre-sterilized, with the possible exception of a container of cell preservative solution. The fluid circuit 10 comprises a separator, generally designated 12, for separating blood into plasma and red blood cells. In the illustrated fluid circuit 10, the separator 12 comprises a spinning membrane separator. However, a centrifugal separator could also be used without departing from the scope of the disclosure. A spinning membrane separator employs relatively rotating surfaces, at least one or which carries a porous membrane. Typically the device employs an outer stationary housing and an internal spinning rotor covered by a porous membrane.

A detailed description of a spinning membrane separator may be found in U.S. Pat. No. 5,194,145 to Schoendorfer, which is incorporated by reference herein. This patent describes a membrane-covered spinner having an interior collection system disposed within a stationary shell. Blood is fed into an annular space or gap between the spinner and the shell. The blood moves along the longitudinal axis of the shell toward an exit region, with plasma passing through the membrane and out of the shell into a collection bag. The remaining blood components, primarily red blood cells, platelets and white cells, move to the exit region between the spinner and the shell and then are typically returned to the donor. A well-known plasmapheresis device utilizing such a spinning membrane separator is the Autopheresis-C® separator sold by Fenwal, Inc. of Lake Zurich, Illinois.

Spinning membrane separators have been found to provide excellent plasma filtration rates, due primarily to the unique flow patterns ("Taylor vortices") induced in the gap between the spinning membrane and the shell. The Taylor vortices help to keep the blood cells from depositing on and fouling or clogging the membrane.

As illustrated, the separator 12 comprises a housing with an inlet 14 at the lower end of the housing (through which blood enters), a first outlet 16 at the upper end of the housing (through which separated red blood cells exit), and a second outlet 18 (through which separated plasma exits).

The fluid circuit 10 also includes a leukocyte reduction filter 20. An exemplary leukocyte reduction filter for red blood cell collection is the BioR™ filter, available from Fresenius Kabi, which utilizes a melt-blown, non-woven polyester fiber for the filter media, in which the fibers have a non-ionic surface coating.

The fluid circuit 10 includes containers of solutions that are used in the procedure. With reference to FIG. 1, the fluid circuit 10 includes a source 22 of solution such as an additive preservative solution that is added to the separated red blood cells and can also be used for priming and rinsing the fluid circuit 10. Adenine-dextrose-mannitol is typical. A source 24 of eluate is provided for back washing the leukocyte filter 20, with saline, and preferably phosphate buffered saline, being a typical eluate.

The fluid circuit also includes empty collection containers for receiving the separated first blood component (red blood cells), second blood component (plasma), and recovered leukocytes. Referring to FIG. 1, a first collection container 26 is provided for receiving leuko-reduced first blood component; a second collection container 28 is provided for receiving the recovered leukocytes; and a third collection container 30 is provided for receiving the separated second blood component.

The collection containers and the containers for the solutions may be made of any suitable material, but are typically flexible plastic pouches or bags.

Flexible plastic tubing defines flow paths between the various components of the fluid circuit. Specifically, a first fluid flow path 32 is provided that is in fluid communication with the inlet 14 of the separator 12. The first fluid flow path is also configured to be connected to a source of the blood that is to be separated. The source may be a container of previously collected whole blood (such as the container 34 seen in FIGS. 2-7). Such a container of previously-collected blood may be pre-assembled with the remainder of the fluid circuit 10, but more likely is connected to the fluid circuit by a sterile connection device or other suitable mechanism at the time of the separation procedure. Alternatively, the flow path 32 may include a vascular access device (not shown) so that it may be directly connected to a donor or patient.

A second fluid flow path 36 provides fluid communication between the first (RBC) outlet 16 of the separator 12 and the inlet 38 of the leukocyte reduction filter 20. A third fluid flow path 40 provides fluid communication between the outlet 42 of the leukocyte reduction filter and the first (RBC) collection container 26.

A fourth fluid flow path 44 provides fluid communication between the source 28 of additive solution and the first fluid flow path 32 (to permit use of the solution for priming and/or rinsing the fluid circuit), while a fifth fluid flow path 46 provides fluid communication between the source 22 of additive solution and the second fluid flow path 36 leading to the leukocyte reduction filter 20 (to combine additive solution with the separated red blood cells).

A sixth fluid flow path 48 provides fluid communication between the source 24 of eluate and the third fluid flow path 40, so as to permit eluate to flow to the outlet 42 of the leukocyte reduction filter 20 to backwash the filter 20. A seventh fluid flow path 50 provides fluid communication between the collection container 28 and the fifth fluid flow path 46 so as to permit the recovered leukocytes and eluate to flow out the inlet 38 of the filter 20 and then sequentially through the second (36), fifth (46) and seventh (50) fluid flow paths and into the container 28. An eighth fluid flow path 52 provides fluid communication between the second (plasma) outlet 18 of the separator 12 and the third (plasma) collection container 30.

Turning to FIGS. 2-7, there is seen a fluid circuit 10 in combination with a reusable durable hardware component 54 comprising a series of pumps, clamps, and sensors (not shown) automatically operated by a programmable controller 56 to control flow through the fluid circuit. While not illustrated, the durable component 54 may also include hangers with associated weight scales for supporting any or all of the containers 22, 24, 26, 28, 30 and 34. As illustrated, the hardware component 54 comprises three pumps. A first pump 58 is associated with the first fluid flow path 32 for delivering fluid to the inlet 14 of the separator 12. A second pump 60 is associated with the second fluid flow path 36 for flowing the separated first blood component (red blood cells) from the first outlet 16 of the separator to the inlet 38 of the leukocyte reduction filter 20. A third pump 62 is associated with the fifth fluid flow path 46 for delivering additive solution to the second fluid flow path 36 to be combined with the separated first blood component (red blood cells) when operated in a first direction, and to deliver the recovered leukocytes and eluate for the inlet 38 of the leukocyte reduction filter 20 to the second (recovered leukocyte) collection container 28. The pumps 58, 60, 62 may be of any suitable construction, such as a peristaltic pump or a flexible diaphragm.

Figure 2:
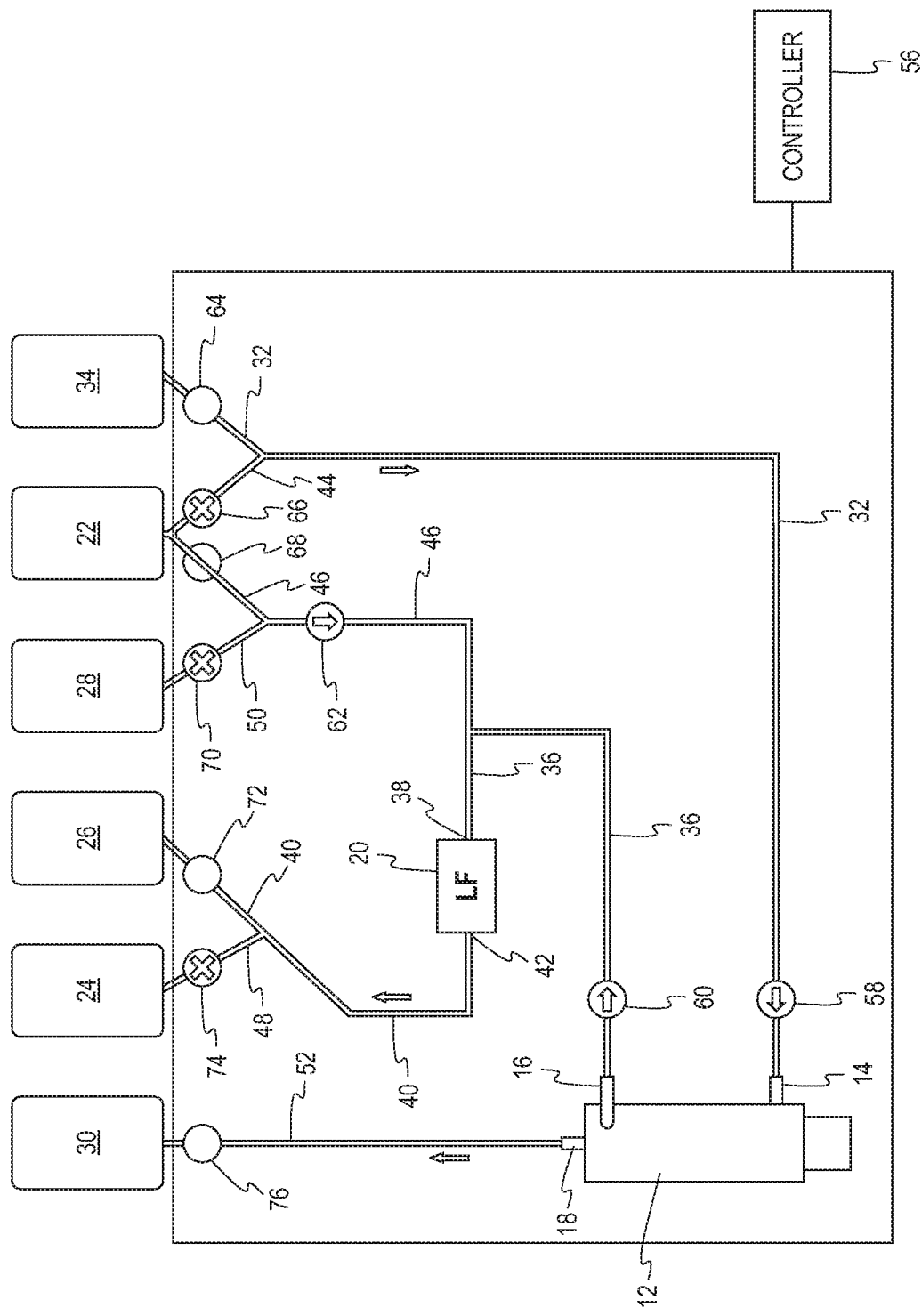
FIGS. 2-4 are schematic views of a first embodiment of a system in accordance with the present disclosure having the single use fluid circuit of FIG. 1 associated therewith, with FIG. 2 illustrating the operation of the system in a blood component collection sub-procedure, FIG. 3 illustrating the operation of the system in the rinse sub-procedure, and FIG. 4 illustrating the operation of the system in the leukocyte recovery sub-procedure.
Figure 3:
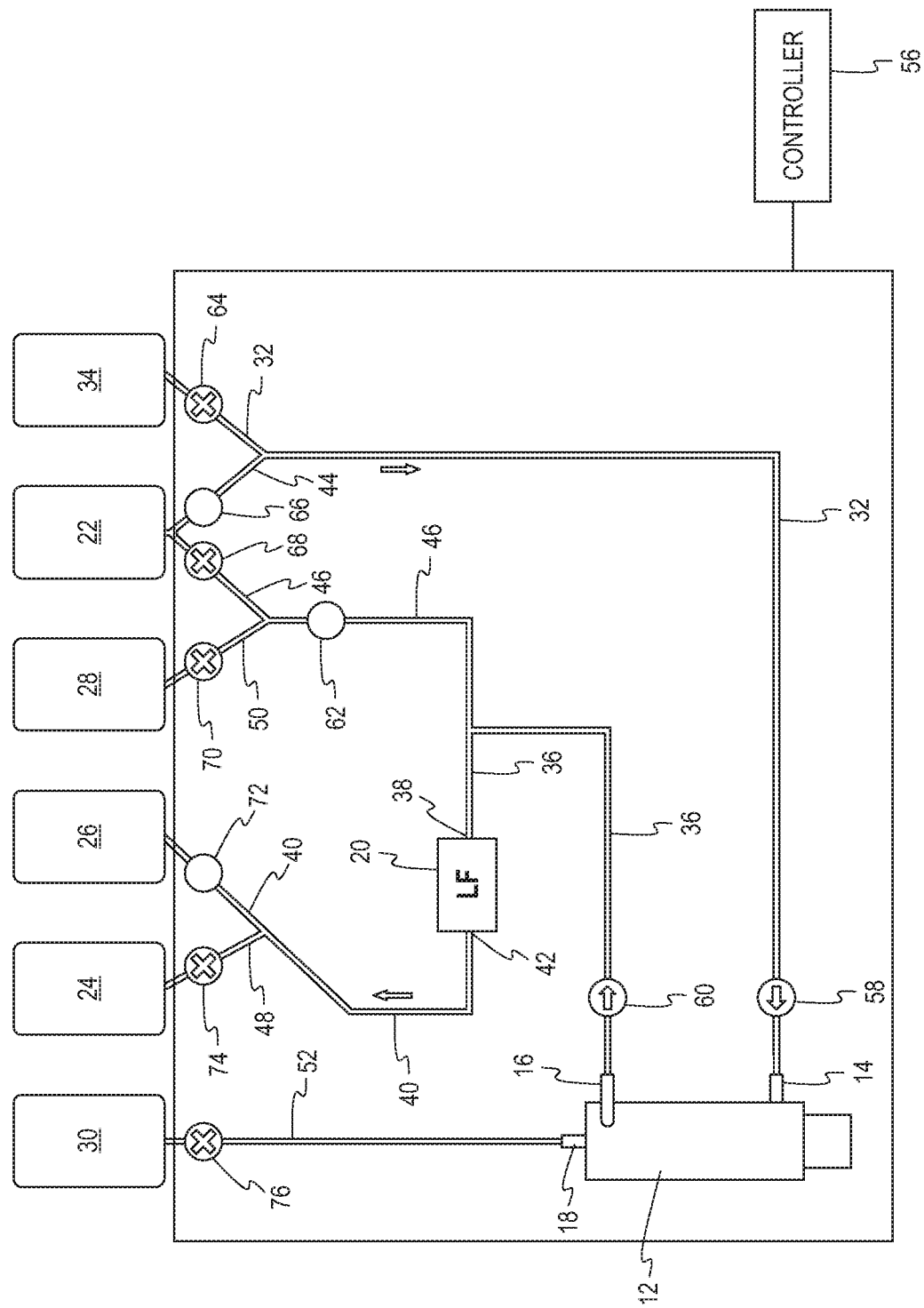
Figure 4:
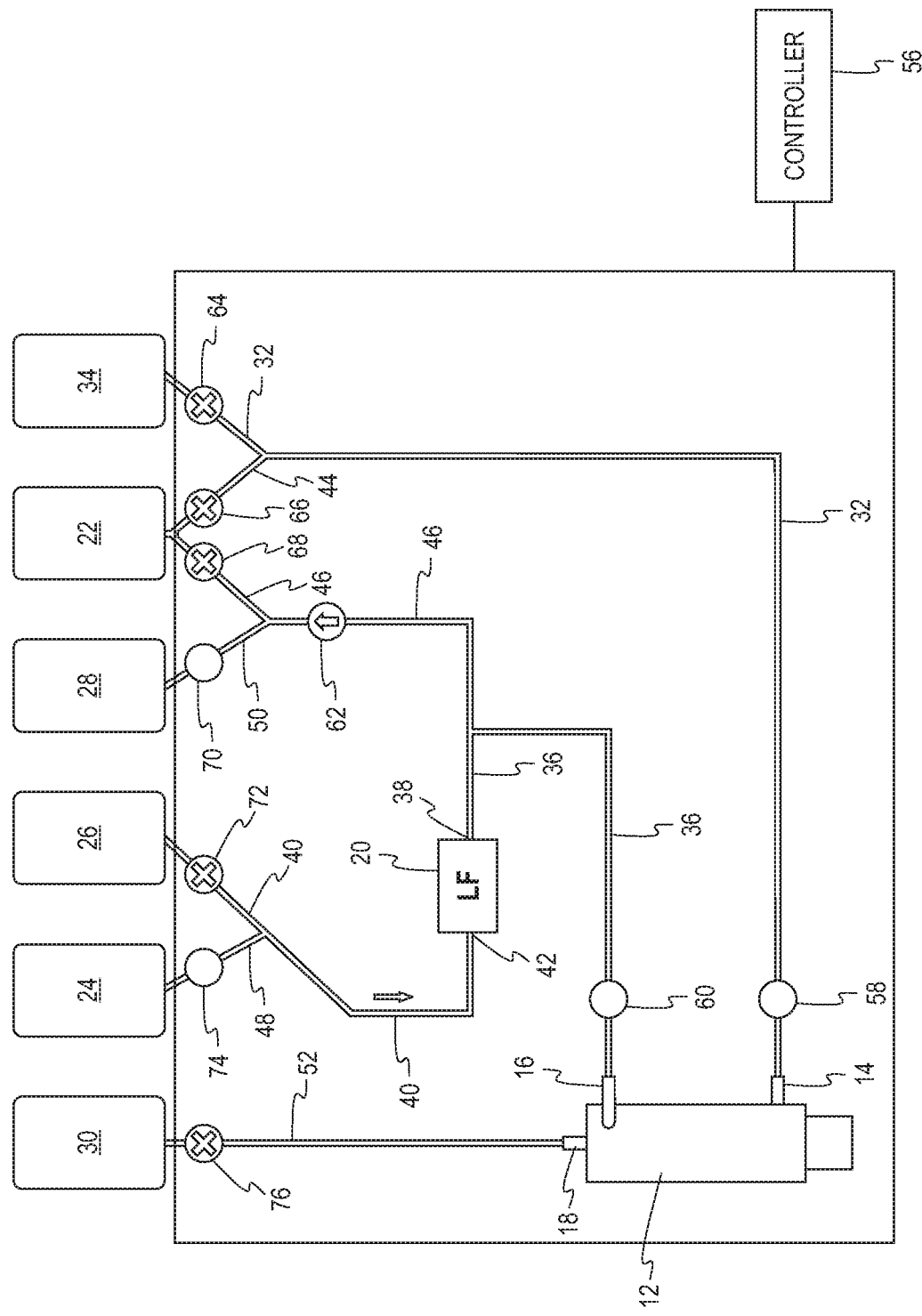

With reference to FIGS. 2-4, the durable module 54 includes a plurality of two-way or binary clamps on the face thereof that engage the tubings of the fluid flow paths to selectively permit or prevent flow through the fluid circuit. As illustrated, seven two-way clamps 64, 66, 68, 70, 72, 74, and 76 are associated with the first, fourth, fifth, seventh, third, sixth, and eighth fluid flow paths 32, 44, 46, 50, 40, 48, and 52, respectively. The clamps are positioned in close proximity to the ports of the containers associated with the flow paths to better control flow into and out of the containers. Specifically, clamp 64 is associated with the first fluid flow path 32; clamp 66 is associated with the fourth fluid flow path 44; clamp 68 is associated with the fifth fluid flow path 46; clamp 70 is associated with the seventh fluid flow path 50; clamp 72 is associated with the third fluid flow path 40; clamp 74 is associated with the sixth fluid flow path 48; and clamp 76 is associated with the eighth fluid flow path 52.

Figure 5:
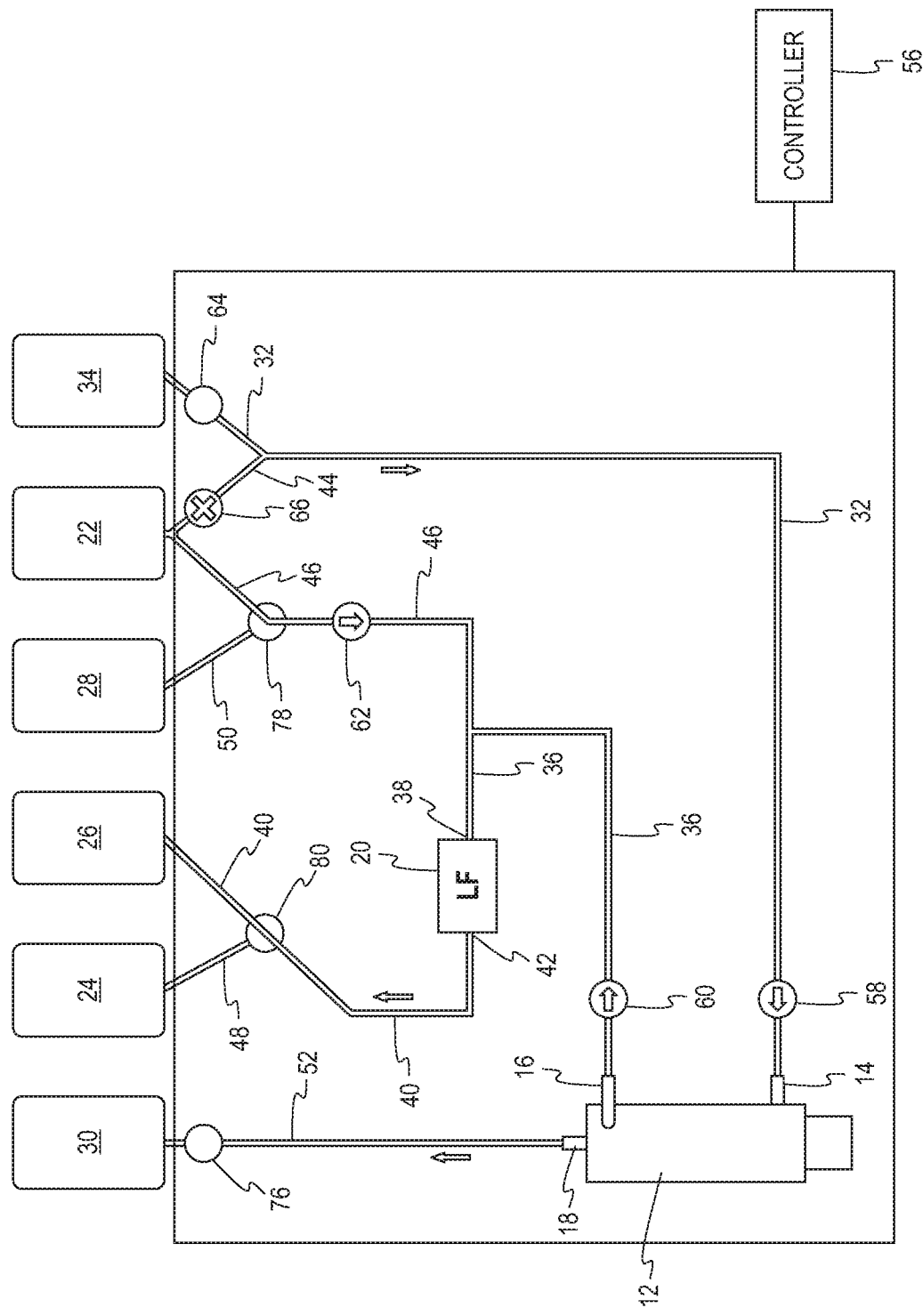
FIGS. 5-7 are schematic views of a second embodiment of a system in accordance with the present disclosure having the single use fluid circuit of FIG. 1 associated therewith, with FIG. 5 illustrating the operation of the system in the blood component collection sub-procedure, FIG. 6 illustrating the operation of the system in the rinse sub-procedure, and FIG. 7 illustrating the operation of the system in the leukocyte recovery sub-procedure.
Figure 6:
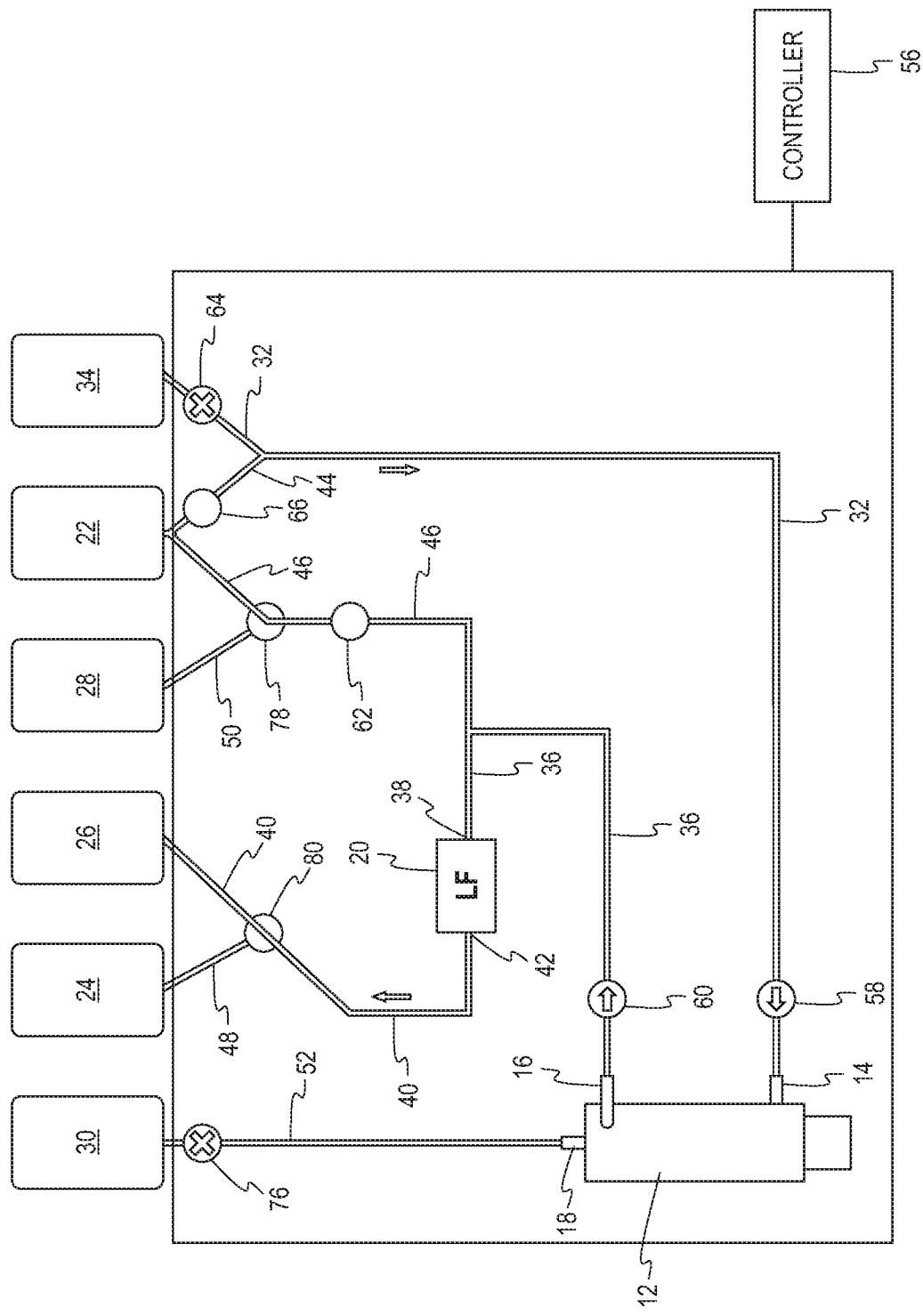
Figure 7:
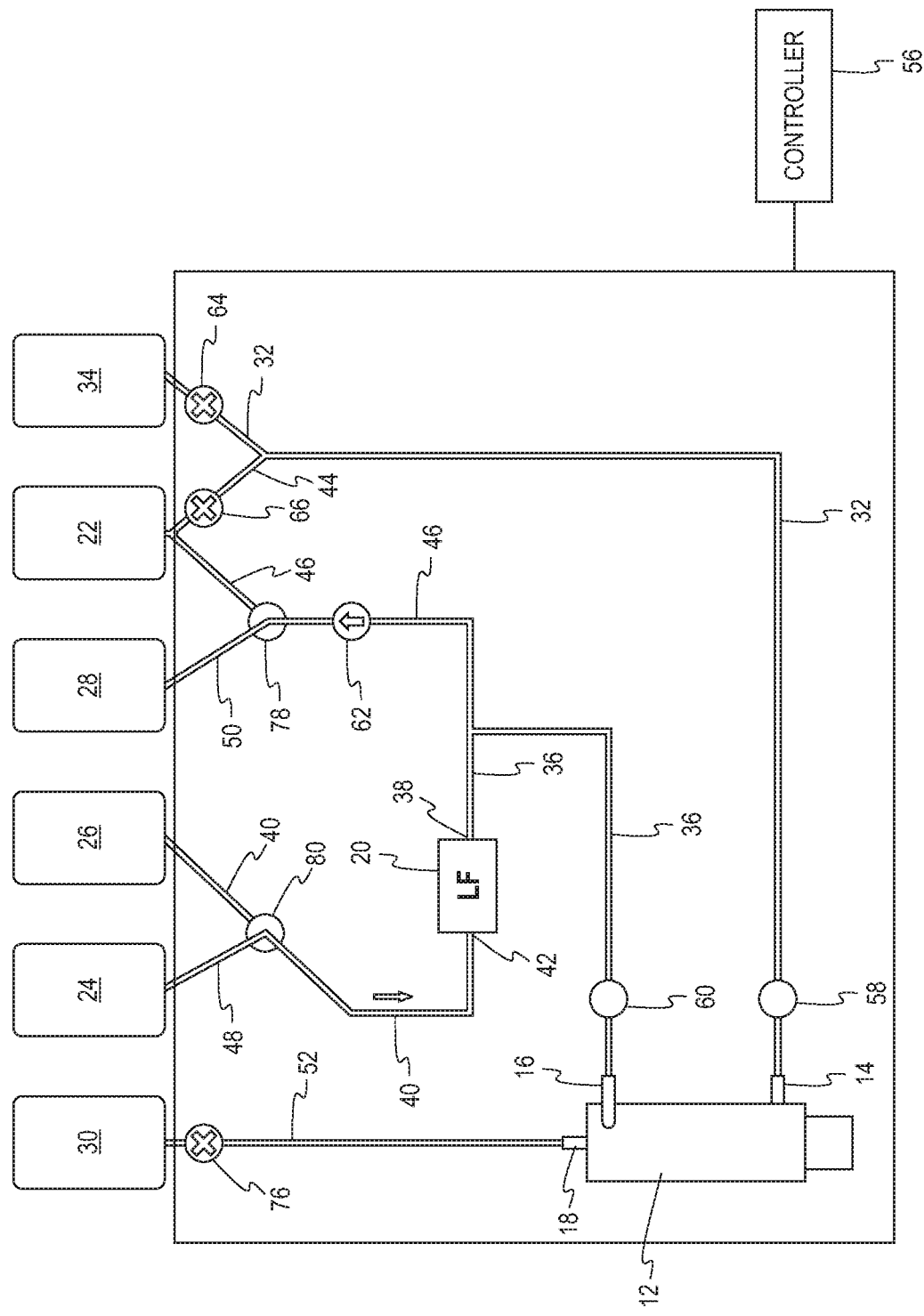

In an alternate embodiment of the durable module, illustrated in FIGS. 5-7, binary clamps 68 and 70 are replaced by a first three-way clamp 78 associated with the juncture of the fifth fluid flow path 46 and the seventh fluid flow path 50, while a second three-way clamp 80, associated with the juncture of the third fluid flow path 40 and the sixth fluid flow path 48, replaces binary clamps 72, 74.

A method for recovering leukocytes in conjunction with the separation of blood into a first blood component (red blood cells) and a second blood component (plasma) using a system such as that set forth above will now be described. As noted above, the method comprises three sub-procedures. The first sub-procedure separates red blood cells from the blood, leukoreduces the red blood cells, and collects the leuko-reduced red blood cells in the first container. The first sub-procedure is illustrated in FIGS. 2 and 5. The second sub-procedure rinses the flow path, using the additive solution. The second sub-procedure is illustrated in FIGS. 3 and 6. The third sub-procedure backwashes the leukocyte-reduction filter with the eluate, and collects the leukocytes recovered from the filter in the second container. The third sub-procedure is illustrated in FIGS. 4 and 7.

In FIGS. 2-7, arrows are used to indicate the direction of flow through the various flow paths of the fluid circuit. For the two-way clamps in FIGS. 2-7, an open circle indicates that the camp is open, thus permitting flow therethrough. An "X" within the circle indicates that the clamp is closed, and that no flow is permitted through the flow path past the clamp. For the three-way clamps in FIGS. 5-7, the flow path is drawn through the center of the circle to indicate the flow paths through which flow is permitted. For the pumps, an arrow is used to indicate the direction of flow caused by the pump. If no arrow is associated with the pump, the pump is not operating and essentially functions as a closed two-way clamp.

With reference to FIG. 2, the first RBC collection sub-procedure is seen. In this part of the procedure, the clamp 64 is opened so that blood flows through the first fluid flow path 32, drawn by operation of the first pump 58, to the inlet 14 of the separator 12. The separator acts to separate red blood cells from plasma, with the plasma flowing through second outlet 18 into the eighth flow path 52 past the open clamp 76 and into the third collection container 30. Separated red blood cells flow from the first outlet 16 of the separator 12 through the second fluid flow path 36, assisted by the operation of the second pump 60. Simultaneously, clamp 68 is opened to permit additive solution to flow through the fifth fluid flow path 46, assisted by the operation of the third pump 62, and into the second fluid flow path 36 downstream of the second pump 60 to be combined with the separated red blood cells. Clamp 66 associated with the fourth fluid flow path 44 remains closed, so that no additive solution flows from the source 22 into the first fluid flow path 32. The combined red blood cells and additive solution flow through the second fluid flow path 36 into the inlet 38 of the leukocyte-reduction filter 20. Leukocyte-reduced red blood cells flow from the outlet 42 of the leukocyte-reduction filter 20, through the third fluid flow path 40 past the open clamp 72 and into the first collection container 26. The clamp 74 associated with the source of eluate 24 remains closed during this part of the procedure. The RBC separation sub-procedure is complete when the source 34 of blood is substantially emptied.

Once the RBC collection sub-procedure is completed, the second rinse sub-procedure may be commenced. As illustrated in FIG. 3, the clamp 76 on the flow path 52 to the third, plasma collection container 30 is closed to prevent any flow into or out of the container 30. Clamps 70 and 74 remain closed, while clamp 72, associated with the first, RBC collection container, remains open. Clamp 64, associated with the source of blood 34 is closed, while clamp 44 associated with the fourth flow path 44 that is connected to the source 22 of additive solution is opened. The third pump 62 is deactivated. Additive solution then flows from the fourth fluid flow path 44 into the first fluid flow path 32 and to the inlet 14 of the separator 12, assisted by the operation of the first pump 58. The additive solution then flows out the first outlet 16 of the separator 12 through the second fluid flow path 36 to the inlet 38 of the leukocyte reduction filter 12, assisted by the operation of the second pump 60. The additive solution (plus any residual red blood cells) then flows out the outlet 42 of the leukocyte-reduction filter 20 through the third fluid flow path 40, past the open clamp 72, and into the first (RBC) collection container 26. The rinse sub-procedure is completed after an appropriate amount of additive solution is flowed through the fluid circuit 10.

The third leukocyte-recovery sub-procedure may commence at the conclusion of the rinse sub-procedure. As illustrated in FIG. 4, clamps 64, 68 and 76 remain closed, clamps 66 and 72 are closed, and clamps 70 and 74 are opened. Operation of the first pump 58 and the second pumps 60 are ceased, so that these pumps essentially act as a closed two-way clamp. Then, the leukocyte reduction filter 20 is backwashed with the eluate. Specifically, eluate is flowed out of the source 24, through the sixth fluid flow path 48, past the open clamp 74, and into the third fluid flow path 40, assisted by the operation of the third pump 62. The eluate then flows into the outlet 42 of the leukocyte-reduction filter 20. Eluate and recovered leukocytes flow out the inlet 38 of the leukocyte-reduction filter 20, through the second fluid flow path 36 and into the fifth fluid flow path 46, again assisted by operation of the third pump 62. The combined eluate and recovered leukocytes then flow from the fifth fluid flow path 46 through the seventh fluid flow path 50, past the open clamp 70 and into the second collection container 28. Once the leukocyte recovery is completed, the clamp 70 is closed.

FIGS. 4-7 illustrate the same sub-procedures as FIGS. 2-4, respectively. The directions of flow through the flow paths and the operation of the pumps 58, 60 and 62 and the clamps 64, 66, and 76 are identical. As noted above, the binary clamps 68, 70 of FIGS. 2-4, are replaced by a first three-way clamp 78 associated with the juncture of the fifth fluid flow path 46 and the seventh fluid flow path 50, while a second three-way clamp 80, associated with the juncture of the third fluid flow path 40 and the sixth fluid flow path 48, replaces binary clamps 72, 74. The three-way clamps are operated to duplicate the operation of the two-way clamps that they replace.

Examples of Different Aspects

Without limiting any of the foregoing, the subject matter described herein may be found in one or more apparatus or methods. For example, in a first aspect, a single-use fluid circuit for recovering leukocytes in conjunction with separation of biological fluid into two or more components is provided that comprises a separator having an inlet for receiving the biological fluid, a first outlet for a separated first component, and a second outlet for a separated second component; a leukocyte reduction filter having an inlet and an outlet; a first fluid flow path in fluid communication with the inlet of the separator and configured to be connected to a source of biological fluid; a second fluid flow path connecting the first outlet of the separator to the inlet of the leukocyte reduction filter; a first collection container for receiving leukocyte-reduced first component; a third fluid flow path connecting the outlet of the leukocyte reduction filter to the first collection container; a source of solution in fluid communication with the first fluid flow path through a fourth fluid flow path and with the second fluid flow path through a fifth fluid flow path; a source of eluate in fluid communication with the third fluid flow path through a sixth fluid flow path; and second collection container in fluid communication with the fifth fluid flow path through a seventh fluid flow path for receipt of recovered leukocytes.

In a second aspect, the separator may be a spinning membrane separator.

In a third aspect, the separator comprises a housing having a top and a bottom, with the inlet adjacent the bottom of the housing and the first and second outlets adjacent the top of the housing.

In a fourth aspect, the solution comprises an additive or preservative solution and the eluate comprises saline.

In a fifth aspect, the fluid circuit further comprises a third collection container and an eighth fluid flow path that provides fluid communication between the second outlet of the separator and the third collection container.

In a sixth aspect, a system for recovering leukocytes in conjunction with separation of a biological fluid comprising blood into a first component and a second component is provided. In a particular aspect, the first component may comprise red blood cells and the second component may comprise plasma. The system comprises: a) a single-use fluid circuit in accordance with any or all of the previous aspects and a durable hardware component. The durable hardware component comprises a plurality of clamps for selectively permitting fluid flow through the fluid circuit, a plurality of pumps associated with selected fluid flow paths for moving fluid through the flow paths, and a programmable controller for automatically selectively opening and closing the clamps and actuating the pumps.

In a seventh aspect, the clamps selectively permit fluid flow from the source of whole blood to the first fluid flow path, from the source of additive solution to the first fluid flow path, from the source of additive solution to the fifth fluid flow path, from the seventh fluid flow path to the fifth fluid flow path, from the third fluid flow path to the first container, and from the sixth fluid flow path to the third fluid flow path.

In an eighth aspect, the clamps comprise two way clamps associated with each of the first, third, fourth, fifth, sixth and seventh fluid flow paths.

In a ninth aspect, a two-way clamp is associated with the eighth fluid flow path.

In a tenth aspect, the clamps comprise first a three-way clamp associated with the juncture of the third and sixth fluid flow paths and a second three way clamp associated with the juncture of the fifth and seventh fluid flow paths.

In an eleventh aspect, the pumps comprise a first pump associated with the first fluid flow path, a second pump associated with the second fluid flow path, and a third pump associated with the fifth fluid flow path.

In a twelfth aspect, a method is provided for recovering leukocytes in conjunction with separation of blood into first and second components. The method uses a system such as that set forth in the aspects above, and comprises producing a leukocyte-reduced first blood component from blood by i) flowing blood through the first flow path to the inlet of the separator, ii) flowing the separated first blood component from the first outlet of the separator through the second fluid flow path and flowing solution from the fifth fluid flow path to the second fluid flow path, iii) flowing combined first blood component and solution through the second fluid flow path to the inlet of the leukocyte-reduction filter, and iv) flowing leukocyte-reduced first blood component from the outlet of the leukocyte-reduction filter through the third fluid flow path to the first collection container. Then rinsing the fluid circuit is achieved by flowing solution through the fifth fluid flow path through the first fluid flow path to the inlet of the separator, out the outlet of the separator through the second fluid flow path to the inlet of the leukocyte reduction filter, and out the outlet of the leukocyte reduction filter through the third fluid flow path to the first container. Recovery of leukocytes from the leukocyte-reduction filter is achieved by flowing eluate through the sixth fluid flow path to the third fluid flow path into the outlet of the leukocyte reduction filter, flowing leukocytes and eluate out of the inlet of the leukocyte reduction filter through the second fluid flow path to the fifth fluid flow path, and from the fifth fluid flow path through the seventh fluid flow path to the second collection container.

It will be understood that the embodiments described above are illustrative of some of the applications of the principles of the present subject matter. Numerous modifications may be made by those skilled in the art without departing from the spirit and scope of the claimed subject matter, including those combinations of features that are individually disclosed or claimed herein. For these reasons, the scope hereof is not limited to the above description, but is set forth in the following claims.

The invention claimed is:

1. A single-use fluid circuit for recovering leukocytes in conjunction with separation of a biological fluid comprising blood into two or more components, comprising:
   i) a separator having an inlet for receiving the blood, a first outlet for a separated first blood component, and a second outlet for a separated second blood component;
   ii) a leukocyte reduction filter having an inlet and an outlet;
   iii) a first fluid flow path having first and second ends, the second end being connected to the inlet of the separator, for introducing blood to the inlet of the separator;

iv) a second fluid flow path consisting of a continuous tubing having first and second ends connected on the first end to the first outlet of the separator and on the second end to the inlet of the leukocyte reduction filter;
v) a first container for receiving leukocyte-reduced first blood component;
vi) a third fluid flow path having first and second ends connected on the first end to the outlet of the leukocyte reduction filter and on the second end to the first container;
vii) a second container including a quantity of additive preservative solution in fluid communication with (i) the first fluid flow path through a fourth fluid flow path having first and second ends connected on the first end to the second container and connected on the second end to the first fluid flow path for flowing additive preservative solution to the separator inlet and from the separator outlet into the second fluid flow path and to the inlet of the leukocyte reduction filter and (ii) with the second fluid flow path through a fifth fluid flow path having first and second ends connected on the first end to the second container and on the second end to the second fluid flow path for flowing additive preservative solution directly through the inlet of the leukocyte reduction filter;
viii) a third container including a quantity of eluate in fluid communication with the third fluid flow path through a sixth fluid flow path having first and second ends connected on the first end to the third container and on the second end to the third fluid flow path for flowing eluate directly into the leukocyte reduction filter outlet, through the leukocyte reduction filter, and out of the leukocyte reduction filter inlet to flush leukocytes from the leukocyte reduction filter, the flushed leukocytes flowing into the second fluid flow path and then into the fifth fluid flow path; and
ix) a fourth container for receipt of recovered leukocytes in fluid communication with the fifth fluid flow path through a seventh fluid flow path having first and second ends connected on the first end to the fourth container and on the second end to the fifth fluid flow path for flowing the recovered leukocytes from the inlet of the leukoreduction filter to the fourth container.

2. The fluid circuit of claim 1 wherein the separator is a spinning membrane separator.

3. The fluid circuit of claim 2 wherein the separator comprises a housing having a top and a bottom, and the inlet is adjacent the bottom of the housing and the first and second outlets are adjacent the top of the housing.

4. The fluid circuit of claim 1 wherein the additive preservative solution comprises a preservative solution and the eluate comprises saline.

5. The fluid circuit of claim 1 further comprising a collection container and an eighth fluid flow path providing fluid communication between the second outlet of the separator and the collection container.

6. A system for recovering leukocytes in conjunction with separation of a biological fluid comprising blood into a first blood component and a second blood component, the system comprising:
the single-use fluid circuit of claim 1; and
a durable hardware component comprising:
i) a plurality of clamps for selectively permitting fluid flow from a source of whole blood to the first fluid flow path, from the second container to the first fluid flow path, from the second container to the fifth fluid flow path, from the seventh fluid flow path to the fifth fluid flow path, from the third fluid flow path to the first container, and from the sixth fluid flow path to the third fluid flow path,
ii) a plurality of pumps associated with selected fluid flow paths for moving fluid through the fluid flow paths, and
iii) a programmable controller for automatically selectively opening and closing the clamps and actuating the pumps.

7. The system of claim 6 wherein each of the first, third, fourth, fifth, sixth and seventh fluid flow paths has a two-way clamp associated therewith.

8. The system of claim 6 wherein the third and sixth fluid flow paths have a first three-way clamp associated therewith, and the fifth and seventh fluid flow paths have a second three-way clamp associated therewith.

9. The system of claim 6 wherein the plurality of pumps comprises a first pump associated with the first fluid flow path, a second pump associated with the second fluid flow path, and a third pump associated with the fifth fluid flow path.

10. A method for recovering leukocytes in conjunction with separation of blood into a first blood component and a second blood component using a system in accordance with claim 6, comprising:
a) producing a leukocyte-reduced first blood component by i) flowing blood through the first fluid flow path to the inlet of the separator, ii) flowing a separated first blood component from the first outlet of the separator through the second fluid flow path and flowing the additive preservative solution from the fifth fluid flow path to the second fluid flow path, iii) flowing combined first blood component and additive preservative solution through the second fluid flow path to the inlet of the leukocyte-reduction filter, and iv) flowing leukocyte-reduced first blood component from the outlet of the leukocyte-reduction filter through the third fluid flow path to the first container;
b) rinsing the fluid circuit by flowing the additive preservative solution through the fourth fluid flow path through the first fluid flow path to the inlet of the separator, out the outlet of the separator through the second fluid flow path to the inlet of the leukocyte reduction filter, and out the outlet of the leukocyte reduction filter through the third fluid flow path to the first container; and
c) recovering leukocytes from the leukocyte-reduction filter by flowing eluate through the sixth fluid flow path to the third fluid flow path into the outlet of the leukocyte reduction filter, flowing leukocytes and eluate out of the inlet of the leukocyte reduction filter through the second fluid flow path to the fifth fluid flow path, and from the fifth fluid flow path through the seventh fluid flow path to the fourth container.

11. The method of claim 10 wherein the fluid circuit further comprises a collection container and an eighth fluid flow path connecting the second outlet of the separator to the collection container, and a second blood component is flowed from the second outlet of the separator through the eighth fluid flow path to the collection container.

* * * * *